United States Patent
Hansmann et al.

(10) Patent No.: US 8,696,588 B2
(45) Date of Patent: Apr. 15, 2014

(54) DEVICE AND METHOD FOR DETERMINING A RESPIRATION RATE

(75) Inventors: Hans-Ullrich Hansmann, Barnitz (DE); Tilman von Blumenthal, Lübeck (DE); Peter Tschuncky, Lübeck (DE); Andreas Hengstenberg, Reinfeld (DE); Frank Mett, Lübeck (DE); Uwe Kühn, Wesenberg (DE); Frank Franz, Lübeck (DE); Kai Kück, Hamburg (DE); Steffen Schmitt, Tremsbüttel (DE)

(73) Assignee: Dräger Medical GmbH, Lübeck (DE)

( * ) Notice: Subject to any disclaimer, the term of this patent is extended or adjusted under 35 U.S.C. 154(b) by 1058 days.

(21) Appl. No.: 11/877,910

(22) Filed: Oct. 24, 2007

(65) Prior Publication Data

US 2008/0139955 A1 Jun. 12, 2008

(30) Foreign Application Priority Data

Dec. 7, 2006 (DE) .................... 10 2006 057 709

(51) Int. Cl.
*A61B 5/08* (2006.01)

(52) U.S. Cl.
USPC ........................ 600/529; 600/534; 600/537

(58) Field of Classification Search
USPC ............................... 600/529–543; 128/204.23
See application file for complete search history.

(56) References Cited

U.S. PATENT DOCUMENTS

| 5,143,078 | A | | 9/1992 | Mather et al. |
| 5,458,622 | A | * | 10/1995 | Alt .................................. 607/15 |
| 5,626,140 | A | * | 5/1997 | Feldman et al. ............. 600/484 |
| 5,876,353 | A | * | 3/1999 | Riff .............................. 600/547 |
| 6,064,910 | A | * | 5/2000 | Andersson et al. ............ 607/20 |
| 6,095,991 | A | * | 8/2000 | Krausman et al. ........... 600/595 |
| 6,171,258 | B1 | * | 1/2001 | Karakasoglu et al. ........ 600/529 |
| 6,261,238 | B1 | * | 7/2001 | Gavriely ...................... 600/532 |
| 6,290,654 | B1 | * | 9/2001 | Karakasoglu ................ 600/529 |
| 6,503,206 | B1 | * | 1/2003 | Li et al. ........................ 600/481 |

(Continued)

FOREIGN PATENT DOCUMENTS

| CA | 2505008 A1 | 5/2004 |
| CA | 02506394 A1 | 11/2005 |

(Continued)

OTHER PUBLICATIONS

"Multi-Sensor Fusion for Robust Computation of Breathing Rate" Tarassenko. Electronics Letters. 38 Issue:22. 1314-1316. Oct. 24, 2002.*

(Continued)

*Primary Examiner* — Navin Natnithithadha
*Assistant Examiner* — Meredith Weare
(74) *Attorney, Agent, or Firm* — McGlew and Tuttle, P.C.

(57) ABSTRACT

A device (1) and a corresponding method are provided for determining and/or monitoring the respiration rate based on measurement with more than one sensor (5, 7, 9, 13, 15). The device may be part of a monitor for determining and/or monitoring the respiration rate. The second and/or additional sensors are different form the first sensor and have a different manor of operation from the first sensor.

16 Claims, 2 Drawing Sheets

(56) References Cited

U.S. PATENT DOCUMENTS

| | | | |
|---|---|---|---|
| 2003/0000522 A1* | 1/2003 | Lynn et al. | 128/200.24 |
| 2003/0100843 A1* | 5/2003 | Hoffman | 600/538 |
| 2003/0187337 A1* | 10/2003 | Tarassenko et al. | 600/300 |
| 2003/0191610 A1* | 10/2003 | Chen et al. | 702/191 |
| 2004/0133087 A1* | 7/2004 | Ali et al. | 600/323 |
| 2005/0027205 A1* | 2/2005 | Tarassenko et al. | 600/529 |
| 2005/0043644 A1* | 2/2005 | Stahmann et al. | 600/529 |
| 2005/0101889 A1* | 5/2005 | Freeman et al. | 601/41 |
| 2005/0234518 A1* | 10/2005 | Heruth et al. | 607/6 |
| 2006/0030764 A1* | 2/2006 | Porges et al. | 600/323 |
| 2006/0094943 A1* | 5/2006 | Van Slyke | 600/323 |
| 2006/0224357 A1* | 10/2006 | Taware et al. | 702/179 |
| 2010/0004552 A1* | 1/2010 | Zhang et al. | 600/529 |
| 2011/0066062 A1* | 3/2011 | Banet et al. | 600/534 |
| 2011/0257489 A1* | 10/2011 | Banet et al. | 600/301 |

FOREIGN PATENT DOCUMENTS

| | | |
|---|---|---|
| DE | 40 11 065 A1 | 10/1991 |
| DE | 41 27 014 A1 | 2/1993 |
| DE | 102004042797 A1 | 5/2005 |
| EP | 0 178 097 B1 | 4/1986 |
| WO | WO 03/051198 * | 6/2003 |
| WO | WO 20050087097 A1 | 9/2005 |

OTHER PUBLICATIONS

"Quatitative Analysis of Qualitative Data." Young, Forrest. Psychometrika. vol. 46, No. 4. Dec. 1981. pp. 357-388.*

"Signal Processing Methods for Non-Invasive Respiration Monitoring." Mason, Laura. University of Oxford. 2002. 174 pages.*

"Measurement of Respiratory Rate with High-Resolution Accelerometer and EMFit Pressure Sensor." Reinvuo et al. IEEE Sensors Applications Symposium. Feb. 7-9, 2006. pp. 192-195.*

Gavriely et al. "Spectral characteristics of chest wall breath sounds in normal subjects." Thorax 1995;50:1292-1300.*

* cited by examiner

DEVICE AND METHOD FOR DETERMINING A RESPIRATION RATE

CROSS REFERENCE TO RELATED APPLICATIONS

This application claims the benefit of priority under 35 U.S.C. §119 of German Patent Application DE 10 2006 057 709.4 filed Dec. 7, 2006, the entire contents of which are incorporated herein by reference.

FIELD OF THE INVENTION

The present invention pertains to a device for determining a respiration rate and pertains to a method for determining a respiration rate as well as to a monitor.

BACKGROUND OF THE INVENTION

The respiration rate is an important indicator of the well-being and the health status of a human being. An illness or state of stress is often reflected by changes in the respiration rate. The monitoring of the respiration rate therefore regularly makes an important contribution to the monitoring of the state of stress and the health status of the person being monitored.

Various respiration rate monitors for use in hospitals as well as outside hospitals are currently known in medicine for monitoring the respiration rate. One example of such a monitor or such a device for monitoring respiration is known from DE 40 11 065 A1.

However, especially for the non-invasive monitoring of respiration, the prior-art devices do not meet the requirements imposed concerning clinical handling, reliability, accuracy and reproducibility of the measurement results. This is due especially to the fact that the devices currently available for monitoring respiration and for measuring the respiration rate are either complicated technically and in terms of design and are felt to be disturbing by the user or the person being monitored, and this is especially true of devices for use outside hospitals and for use by mobile, i.e., not bedridden patients, or these devices have a high sensitivity to artifacts.

SUMMARY OF THE INVENTION

The object of the present invention is therefore to make possible the reliable measurement of the respiration rate of a person. Another object of the present invention is to ensure that the person in question is compromised during the measurement of the respiration rate to the lowest extent possible.

A device for determining the respiration rate is thus provided according to the present invention, wherein at least two different sensors are used for determining the respiration rate, and these sensors determine the respiration rate in at least two different ways.

Thus, monitoring or measurement of the respiration rate can also be ensured according to the present invention when a sensor or a measurement method cannot provide sufficiently accurate or reliable data on the respiration rate because of artifacts and/or external circumstances. There is such a case with conventional devices or, e.g., when a motion-dependent sensor responds to motions of the rib cage, which were not caused by the respiration. However, the data may also be inaccurate in case of shallow breathing, which is not recognized as breathing by the motion-dependent sensor. There may be a comparable situation when a noise-dependent sensor also counts alleged breaths in an unacceptable manner because of ambient noise. This may happen when the user of the device is jogging or when the user of the device is running.

When a sensor does not permit counting of the respiration rate—or the determination of the respiration rate in general—over a certain period of time because of an artifact as described above or another artifact, the respiration rate can nevertheless be advantageously determined according to the present invention by resorting to at least one other sensor. Thus, unlike in the state of the art, it is possible according to the present invention to nevertheless obtain a measurement result for the respiration rate in case of failure of one sensor.

Another advantage of the device according to the present invention is that by using more than one sensor, the reliability of the measurement as a whole can be checked. Thus, an alarm or even the outputting of no value for a respiration rate whatsoever may be provided when, e.g., a sensor determines an erroneous value, which conflicts with values of one or more other sensors. The user of the device according to the present invention (a user can be defined according to the present invention either as the user of the device or the care provider of the user or a physician) therefore knows that he or she must not rely on the measurement of the respiration rate at such a point in time because at least one sensor is producing an erroneous result.

Provisions may also be made according to the present invention for discarding the non-agreeing value and thus for not taking that value into account for the determination of the respiration rate when the values of the respiration rate determined by, e.g., two or more sensors agree or essentially agree and the value from another sensor does not agree. The respiration rate is thus stated as a value ascertained on the basis of different observations, which leads to increased reliability in the determination of the respiration rate.

These sensors may be designed according to the present invention as:

Sensors that measure the expansion of a chest belt on the basis of changes in resistance, as described in EP 0 178 097 B1, wherein the respiratory excursion of the chest can be measured and/or the respiratory movement of the abdominal cavity can be measured by means of an abdominal belt;

Sensors that measure the change in the impedance of a coil due to the changed thoracic and/or abdominal diameter. The chest belt has a suitable coil. A preamplifier (oscillating circuit) may be provided to increase the robustness of the signal;

Sensors that determine the impedance of the thoracic cavity by a voltage drop of an alternating current sent through the thoracic cavity with the use of electrodes, for which electrocardiogram (ECG) electrodes possibly already present may also be used;

Sensors that are used for ECG leads to determine the beats of the frequency of movement of the thoracic cavity, which beats are generated by the respiration-related change in the position of the cardiac axis, as is described in CA 0 2506 394 A1. The mechanical movement of the thorax during the respiratory movement rather than the gas exchange that has taken place is essentially used for this;

Sensors that measure the change in pressure in the thorax during respiration based on the transmission of respiration to the vascular system by means of plethysmography. The respiration rate can be recognized as a slow vibration based on the expansion of the vessels. This method is especially suitable for vessels located close to the heart;

Sensors that measure the breath sounds. A microphone sensor can pick up the breath sound in the vicinity of the inlets to the airways, as is described in U.S. Pat. No. 5,143,078;

Sensors that measure the bone conduction (acceleration) on the body, e.g., at the ear or on the neck, as described in CA 2 505 008 A1;

Sensors that measure the respiratory movement by means of acceleration pick-ups on the chest, neck or ear;

Sensors that determine a periodic cooling as a breath signal by means of a heated resistor temperature sensor in the vicinity of the inlets to the airways (anemometry);

Sensors that determine a periodic temperature change as a respiration signal by means of a non-heated resistor temperature sensor in the vicinity of the inlets to the airways;

Sensors that measure the gas exchange that has taken place with $CO_2$ as the metabolite as $CO_2$ sensors in the vicinity of the inlets to the airways (optionally by means of a suction system);

Sensors that measure the reduced $O_2$ content as a sign of a metabolism taking place as $O_2$ sensors in the vicinity of the inlets to the airways (optionally by means of a suction system); or Sensors that measure a humidity parameter (e.g., a change in dew point) in the vicinity of the inlets to the airway).

Depending on the goal of monitoring the respiration rate (the device according to the present invention—just as the method according to the present invention—can be used to determine and monitor the respiration rate in patients as well as in healthy subjects, e.g., athletes, or for bio-feedback) and the required mobility, different combinations of sensors and the corresponding combinations of measurement methods may be meaningful. They are therefore also covered by the present invention.

Thus, different sensors, whose advantages and drawbacks complement each other, can be preferably used together in the device according to the present invention. The advantage associated herewith is that, e.g., in case of a disturbance in the measurement of the respiration rate by a sound-sensitive sensor due to ambient noise, measurement of the respiration rate can still be possible by a motion sensor.

Furthermore, it is possible to select sensors whose measuring sites make possible, e.g., a common access (e.g., at the ear only or on the upper body only, etc.). The latter represents a facilitation and simplification for the user in putting on, using and removing the device and hence an advantage according to the present invention.

Two, three or more different methods can be used according to the present invention to determine and/or measure the respiration rate and a corresponding number of sensors can be used. Thus, the present invention is not limited to certain combinations or a certain number of sensors and ways of measurement. The present invention is also not limited to the above-mentioned sensors. The respiration rate measurement may rather also be carried out in any other way of determining the respiration rate known to the person skilled in the art and also with sensors not mentioned here.

Besides additional sensors of another design, the device according to the present invention may also have more than only one sensor of a particular design. This may be advantageous, e.g., when a sensor of this particular design is prone to failure. The device according to the present invention has increased reliability of operation in this case even in case of failure of one sensor.

The respiration rate of the user of the device is thus determined according to the present invention such that the different respiration rates measured by different sensors are taken into account. The taking into account of more than only one respiration rate makes possible, especially based on the different methods used for the measurement, the more accurate determination of the actual respiration rate, because the effect of erroneously measured respiration rates by means of individual sensors is effectively mitigated. Sliding or dynamic averages of all measured or determined respiration rates, but also other statistical averaging methods, such as the gaussian distribution, the minimization of the sum of the mean squared errors, discarding of the aberrations, and the sliding averaging for past quality values are covered by the present invention. This statistical correction or averaging may take place via the sensors at one point in time. However, it may also take place over the time curve of individual signals and/or all measured signals.

"Determination of the respiration rate" covers according to the present invention not only a measuring operation. Measurement along with further processing, filtering, comparison, etc., of signals, which will lead to a usable respiration rate value only thereafter, are also covered by the present invention.

As was already noted above, the present invention pertains both to the determination and/or monitoring of the respiration rate of a patient in the conventional sense of an ill person and in healthy subjects for monitoring a training schedule during sports activities or the like. The present invention is not, of course, limited to use in humans. The respiration rate of animals can also be monitored by means of the present invention. The present invention may, furthermore, be associated with the determination or measurement of other parameters. Thus, an Electrocardiogram (ECG) lead may be performed, the tidal volume can be determined, the heart rate may be determined, etc., at the same time. Sensors that are already provided for the determination of the respiration rate are advantageously used herefor.

Thus, in a preferred embodiment, the device according to the present invention has at least one means for setting or determining at least one quality value for at least one respiration rate determined by means of one of the sensors. Provisions are therefore made in this embodiment according to the present invention for determining an indicator of the reliability of the signal or respiration rate in question for a respiration rate determined by a sensor. This indicator of the reliability or loadability of the signal or of the respiration rate determined is called the "quality value" according to the present invention. This quality value can be obtained, e.g., by balancing of the respiration rate determined with quality ranges or stored standard data or the like, which were defined in advance, or by any other plausibility check. However, the quality value can also be determined as a function of or in proportion to other, likewise determined signals of the same user. The quality value of a signal or of the respiration rate determined herefrom thus indicates whether the respiration rate determined by the sensor corresponds to the actual respiration rate with sufficient reliability or whether it comes close to this at least with a manageable uncertainty. This quality value is used for quality control and can be advantageously used in different ways.

The quality value may be determined in another special way that appears suitable to the person skilled in the art. In case of a plethysmograph, a quality value of the respiration rate measured by plethysmography can be derived, e.g., on the basis of the wave shape, the amplitude and the frequency spectrum and the signal-to-noise ratio.

Furthermore, it is recognizable to the person skilled in the art that the quality value does not have to be determined in the same manner for each respiration rate determined by means of a sensor. Different procedures may be provided here.

In another, likewise preferred embodiment, the device according to the present invention has a means for determining the respiration rate by taking into account at least two respiration rates determined by means of at least two different sensors. Moreover, the quality values of the respiration rates determined with one or more sensors are taken into account by means of this means in this embodiment.

Thus, a respiration rate of the user is determined in this embodiment such that the different respiration rates measured by different sensors and the quality values thereof (or at least one such quality value) are taken into account. The taking into account of the quality values for every "individual" respiration rate of every sensor leads to an advantageous increase in the qualitative information value of the "overall" respiration rate determined over the sensors taken into account. The quality value can be taken into account according to various mathematical procedures known to the person skilled in the art such that the respiration rate of a sensor, to which a lower or poorer quality value was assigned, has a lower or weaker input to the overall respiration rate than do respiration rates of other sensors with higher or better quality values.

The quality value can be stated as a factor between (including) 0 and (including) 1, and in case of a factor of 0, it causes that the corresponding respiration rate value is not taken into account in the determination of the user's "overall" respiration rate at all. By contrast, the corresponding respiration rate is included in the further determination to the full extent in case of a factor of 1. The corresponding respiration rates are likewise included in the determination proportionally or they are likewise not taken into account in case of factors between 0 and 1. An example will be explained in detail below.

Quality values from measurements with different sensors can also be taken into account further with different weights. This makes allowance for the circumstance that a sensor can consistently always yield more reliable results than another sensor and a respiration rate determined with it shall therefore also always be included in the calculation or determination of the respiration rate more strongly.

In another preferred embodiment, the device according to the present invention has a means for displaying at least one such quality value. The quality or reliability of the respiration rate considered with a certain quality value is advantageously easy to see in this embodiment, and the user or the attending physician can themselves infer the reliability of the correctness of the value of the measured respiration rate. As a consequence of this, the user can also check the mode of operation of the sensors and especially the arrangement thereof on or in relation to the body. Thus, a sound-sensitive sensor can yield an incorrect count simply because it has slipped such that it chafes, for example, the shirt collar and misinterprets the noises generated hereby.

In another preferred embodiment, the device also has at least one evaluating sensor, which shall display mainly information on the quality or reliability of the correctness of the value of the respiration rate measured by means of this sensor.

Thus, a quality value of, e.g., a respiration rate determined by means of an expansion sensor of a chest belt can be obtained, among other things, by balancing of signals of a motion sensor. The signals sent by the motion sensor can indicate, e.g., that the respiration rate measured by means of the expansion sensor is distorted because of increased physical activity (such as during sports activity). An appropriately poorer quality value is correspondingly assigned to such a sensor.

By using at least one such evaluating sensor, it is, furthermore, advantageously possible, e.g., to infer the necessity to trigger an alarm. Thus, a fit of coughing of the user or the user's physical activity may change the measured respiration rate such that a falsely high respiration rate is displayed in the normal case or an alarm would have to be triggered. The simultaneous determination of the physical activity or the detection of a fit of coughing by one or more additional sensors used for this purpose, such as a motion sensor, can be used to determine the quality value and thus used to correctly assess the value and reliability of a respiration rate measured during the fit of coughing. Such an evaluating sensor can measure according to the present invention, e.g., as a motion sensor, the acceleration to recognize and possibly suppress artifacts caused by motion of the user and thus make it possible to infer the user's physical activity.

The present invention is accomplished, furthermore, by a method. Since the advantages that can be achieved herewith correspond to those described above in full measure, reference is made here to the advantages discussed above to avoid repetitions.

The present invention will be explained in more detail below on the basis of the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
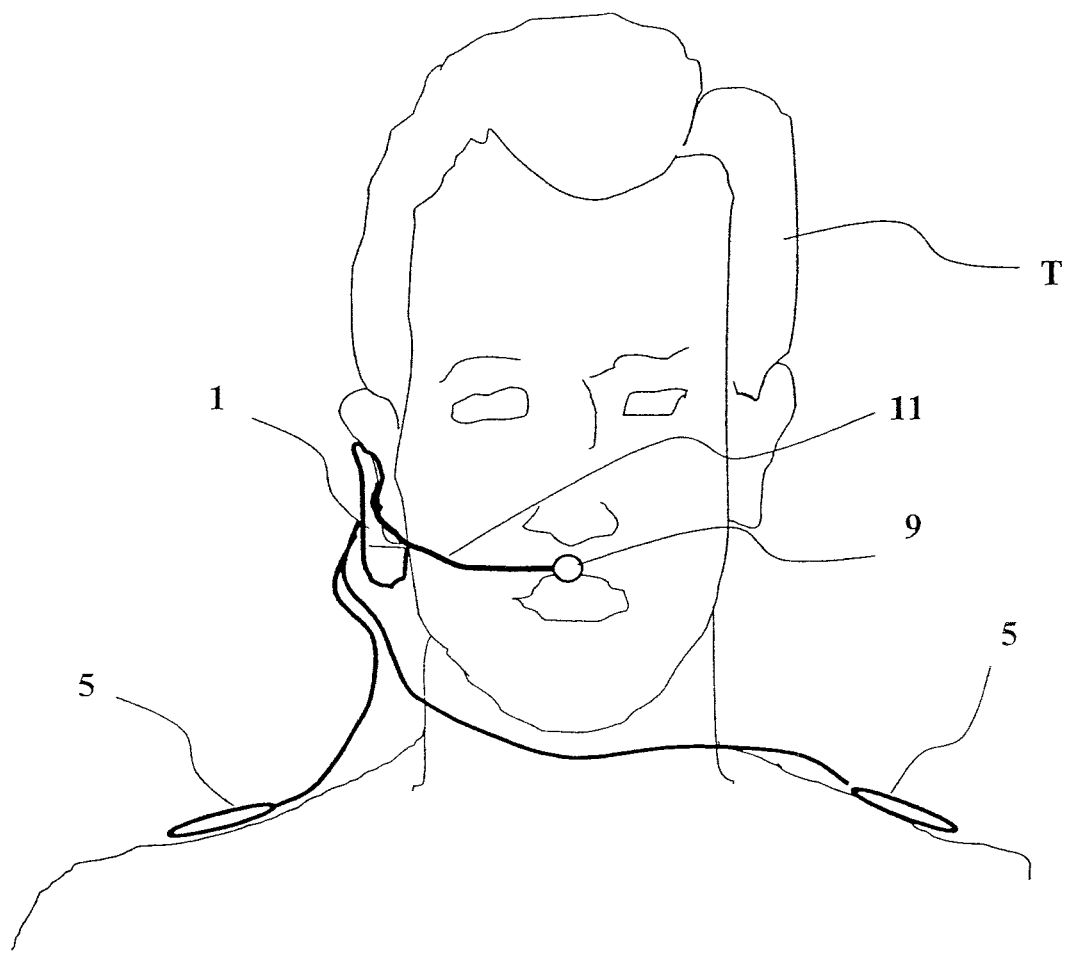
FIG. 1 is a schematic view of a monitor according to the present invention.

Referring to the drawings in particular, FIG. 1 shows a monitor 1, which communicates with the ear and the shoulders as well as an area below the nose of a user T. The monitor 1 is similar to a mobile radio headset. The monitor 1 comprises an energy supply of its own (not shown), a control unit, a communication unit, as well as the sensors provided as an example in this embodiment for determining the respiration rate of the user T.

In this exemplary embodiment of the monitor 1 according to FIG. 1, the monitor has two cable-bound electrodes 5, which are arranged at the two shoulders/collarbones of the user T. The monitor 1 may comprise, furthermore, an ECG amplifier for the electrodes 5. The monitor 1 has, furthermore, an acceleration pick-up 7, which is designed as a three-dimensional motion pick-up in this embodiment. Furthermore, a thermal conductivity sensor 9 is provided on a strap 11 between the mouth and the nose of the user T. An infrared receiver 13 is provided in the ear of the user T for measuring the eardrum temperature. Furthermore, a sensor 15 is provided, which is suitable for use as a transflectory sensor for two-channel (radio (R) and infrared (IR)) photoplethysmography in this embodiment. The sensors 5, 7 and 9 detect information on the user T, from which the respiration rate can be determined. The sensor 15 is also capable of transmitting information on the respiration rate. However, provisions may be made for reasons of saving energy for the sensor 15 not being operated continuously but only during an on-time of, e.g., less than 10% of the time. Thus, it preferably supplies only a few pulse cycles over every x minutes. The power consumption can thus be reduced to the extent that a sufficiently long battery life can be reached even with cosmetically inconspicuous batteries, which are accommodated in the monitor and are therefore worn at the ear. Batteries of this type may be of the zinc-air round cell type (IEC PR48, hearing aid size 13). Comparable batteries may also be used herefor.

In case of this isolated, short-term use of the photoplethysmography sensor 15, this is sufficient for making possible a stable calculation of the oxygen saturation with only a small amount of artifacts. Should the respiration rate measured by means of the sensors 5, 7 and 9 not be expressive enough, especially in view of the particular quality values of the respiration rate, the sensor 15 may also remain turned on continuously over several minutes (e.g., during an on-time of one msec at 200 Hz) and thus make a contribution to the determination of the respiration rate at the expense of increased power consumption.

Sensor 5 amplifies the electric potentials of the two ECG electrodes, which are preferably positioned at the shoulders or in the collarbone regions. The signal obtained from these electrodes is filtered, for which a high-pass filter of 0.05 Hz and a low-pass filter of 10 Hz can be used. The signal received contains, on the one hand, the heart rate (pulse) in the range of approximately 1 Hz to 3 Hz (as a cycle frequency, the signal contains far greater frequency components) with an amplitude of approximately 0.2 mVSS (before amplification). The signal contains, in addition, the respiration rates with approximately 0.1 Hz to 0.5 Hz at an amplitude of 0.04 mV. Both signal components can be recognized by separating the signal contents by means of a fast Fourier transformation method, autocorrelation or an adaptive variable-frequency filter. The assumption that the two frequencies cannot change at any desired rate applies to each possible separation method. If the two frequencies are identified, it is also possible to calculate an amplitude distance from the adjacent or other frequencies being considered. A signal-to-noise ratio S/N is formed from the ratio of the useful signal amplitude (voltage U) to the other amplitudes as follows:

$$S/N_{respiration} = 10 \log(U_{respiration}/U_{adjacent\,frequency}) \text{ and}$$

$$S/N_{heart} = 10 \log(U_{heart}/U_{adjacent\,frequency}).$$

The mean value from $S/N_{respiration}$ and $S/N_{heart}$ for S/N is the quality value for sensor 5.

Sensor 7 is a microstructured acceleration pick-up in this embodiment according to FIG. 1, whose mass deflection is measured capacitively. The sensor contains three such arrays in order to make possible an independent three-dimensional measurement. Sensor 7 is positioned directly in the auditory canal and can follow the motion of the bone or the tissue surrounding it. The acceleration pick-up 7 can be uncoupled from the housing for this. According to another technical solution herefor, the entire monitor 1 is designed as a monitor with such a small weight that uncoupling is not necessary to follow the higher frequencies (up to 10 Hz).

The analysis and the formation of the quality value of the acceleration pick-up 7 is performed analogously to the methods described in connection with sensor 5. However, this sensor or acceleration pick-up 7 also provides information from which the activity of the user can be inferred. This is especially advantageous in case of users who are moving about freely, in order to obtain information on the physical exercise of these users in terms of work and motion. The extent of the user's physical activity can also be used to shift the upper limit value for triggering an alarm and represent increased tolerance.

The thermal conductivity sensor 9 is designed in this embodiment according to FIG. 1 as a very small temperature-dependent platinum resistor (PT100). This thermal conductivity sensor 9 is located at the tip of a strap 11, which protrudes into the area of the upper edge of the mouth. The thermal conductivity sensor 9 should be ideally located 3 cm in front of the upper lip. The resistor can be heated with a low measuring current and adjusted to a temperature of approximately 10 K above the ambient temperature. To avoid any risk to the user because of the temperature of the thermal conductivity sensor 9, this sensor has a very low heat capacity. This is also advantageous for the desired, short response time. The heat dissipation is increased during the breath because of the tidal volume flow, which partially also sweeps over the thermal conductivity sensor 9. The temperature and the resistance value thereupon decrease. The current that is necessary to maintain the thermal conductivity sensor 9 at the temperature to be stabilized measurably increases, by contrast, corresponding to the increased heat dissipation. The heat dissipation of the thermal conductivity sensor 9 is approximately 10 mW without an appreciable velocity of flow. If a signal, which contains a sufficient signal distance from noise signals, is generated with this excess temperature, the excess temperature can be reduced, which results in a reduction in power consumption, until the S/N ratio becomes too poor. The excess temperature can also be increased comparably in case of other signals of a lower quality if no other sensors, which are likewise used, are able to provide a sufficient quality.

The strap 11 may be designed such that it can be folded up in order to prevent the user from being hindered during certain activities or in certain environmental states. The thermal conductivity sensor 9 of the strap 11 may be designed such that it is turned off automatically when the strap 11 is moved into an "inoperative position" to prevent the user T from being hindered or exposed to risks as well as to prevent erroneous respiration rate measurements.

The sensor 13 is designed as a receiver for infrared radiation in this embodiment. It has a receiver surface and a means for measuring the temperature difference of this surface against the housing by means of thermocouples (chains). An emission factor and the housing temperature are needed for determining the temperature of the radiating surface (the eardrum in this case). The emission factor may be assumed to be constant. The housing temperature is determined by means of conventional temperature sensors. The housing may have a good thermal coupling with the external components of the monitor 1 and a comparatively poor coupling with the auditory meatus. As a result, the greatest possible temperature difference is obtained between the radiating surface and the receiving surface, as a result of which a higher radiation capacity is obtained.

The control unit of the monitor 1 calculates the individual quality values Q1, Q2, Q3 and Q4 and integrates the value for the respiration rate $F_{ECG}$ (from ECG sensor 5), $F_{accel}$ (from microstructured acceleration pick-up sensor 7), $F_{temp}$ (from thermal conductivity sensor 9) and $F_{plesmo}$ (from photoplethysmography sensor 15) corresponding to the quality values in a weighted form as follows in an example:

$$F_{breathing} = (Q1*F_{ECG} + Q2*F_{accel}1 + Q3*F_{temp} + Q4*F_{plesmo})/(Q1+Q2+Q3+Q4).$$

If the individual respiration rates $F_{ECG}$, $F_{accel}$, $F_{temp}$ and $F_{plesmo}$ differ greatly from each other (e.g., by more than 20%), the frequency to which the highest quality value has been assigned will be processed further in a special embodiment of the above integration of the individual respiration rates into $F_{respiration}$.

Figure 2:
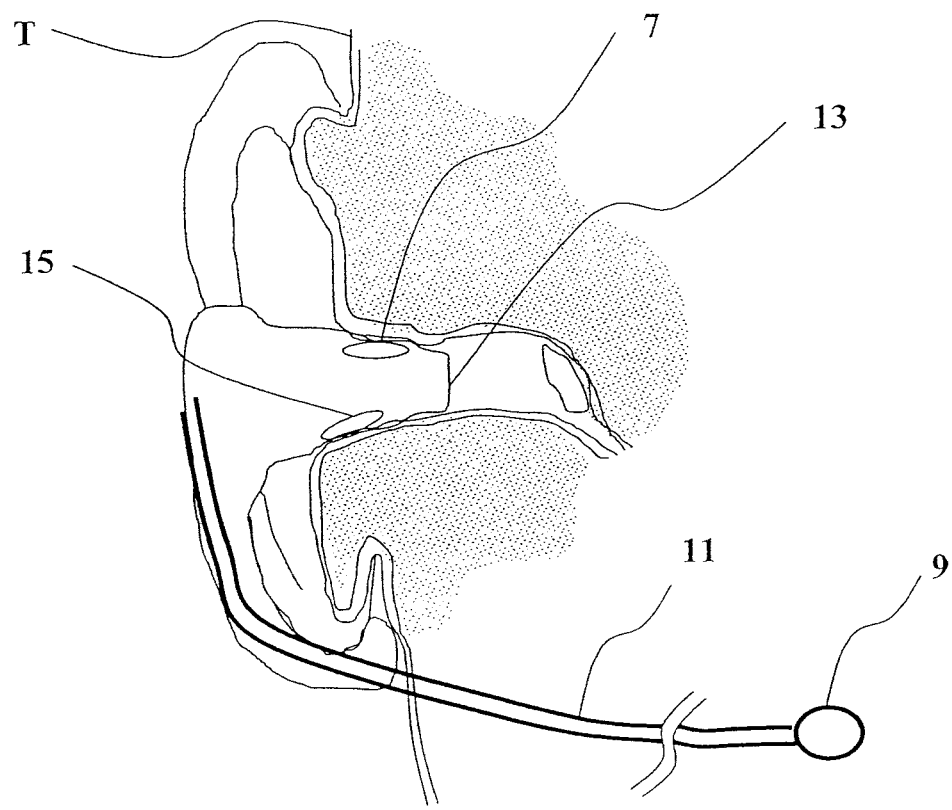
FIG. 2 is a detail view of the monitor according to FIG. 1.

FIG. 2 is a detail of the monitor 1 from FIG. 1 and shows a frontal section through the auditory meatus.

Figure 3:
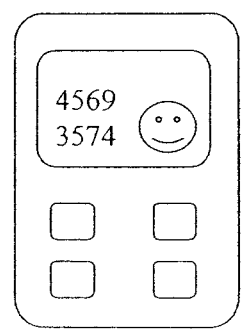
FIG. 3 is a communication unit of the monitor according to FIGS. 1 and 2.

FIG. 3 shows a communication unit of the monitor according to FIGS. 1 and 2. This communication unit includes a display means for displaying quality values and/or respiration rates. It may have radio connection to the monitor. However, it may also be connected by cable.

Thus, the present invention provides, for the first time ever, a device and a corresponding method for determining and/or monitoring the respiration rate based on measurement with more than one sensor. Moreover, it provides a monitor for determining and/or monitoring the respiration rate.

While specific embodiments of the invention have been shown and described in detail to illustrate the application of the principles of the invention, it will be understood that the invention may be embodied otherwise without departing from such principles.

What is claimed is:

1. A method for determining a respiration rate of a subject, the method comprising the steps of:
   measuring a first estimation of the respiration rate in a first way with a first sensor;
   measuring a second estimation of the respiration rate in a second way with a second sensor, said first sensor and said second sensor sensing a different physical characteristic;
   setting by means of a control unit one quality value for each of the first and second estimations of the respiration rate;
   determining a difference by means of the control unit between said first and second estimation of the respiration rate;
   determining by means of the control unit if said difference is greater or less than 20%;
   if said difference is less than 20%, then determining by means of the control unit a third estimation of the respiration rate of the subject by use of weighted averaging based on the first and second estimations of the respiration rate and their respective quality values; and
   if said difference is greater than 20%, then choosing one of the first and second estimations of the respiration rate with the highest quality value as an actual respiration rate of the subject.

2. A method in accordance with claim 1, further comprising the step of:
   displaying one of said set quality values.

3. A method in accordance with claim 1, further comprising:
   providing an evaluating sensor for said measuring of the present activity;
   evaluating the estimations of the respiration rate determined by said first and second sensors by means of said evaluating sensor.

4. A method in accordance with claim 1, wherein:
   said determining of said quality value includes measuring a signal to noise ratio of one of said first and second sensors, and using said signal to noise ratio to set a respective said quality value.

5. A method in accordance with claim 1, wherein:
   said determining of said quality value includes measuring movement of the subject that would interfere with the measuring of one of the first and second sensors, said determining of said quality value using the measurements of movement to set a respective said quality value.

6. A monitor for a subject, the monitor comprising:
   a first sensor for sensing one or more physical characteristics relating to the subject for determining a first estimation of a respiration rate of the subject;
   a second sensor for sensing one or more physical characteristics relating to the subject for determining a second estimation of the respiration rate of the subject, said second sensor being at least one of a different form of sensor from said first sensor, sensing a different physical characteristic from said first sensor and having a different manner of operation from said first sensor;
   a quality value setting means for setting a quality value for each of said first and second sensors; and
   a control unit for receiving signals from said first sensor and said second sensor to selectively provide the respiration rate of the subject based on physical characteristic sensing by one or both of said first sensor and said second sensor, and by each of said quality values,
   wherein said control unit is configured to selectively provide the respiration rate by determining a difference between said first and second estimation of the respiration rate; determining if said difference is less than or greater than 20%, if said difference is 20% or less, then determining a third estimation of the respiration rate by use of weighted averaging based on the first and second estimations of the respiration rate and respective said quality values; and if said difference is greater than 20%, then choosing the one of the first and second estimations with the highest quality value as an actual respiration rate of the subject.

7. A monitor in accordance with claim 6, further comprising an evaluating sensor for evaluating at least one of said estimations of the respiration rates based on physical characteristic sensing by one or both of said first sensor and said second sensor, said evaluating sensor being separate from said first and second sensors.

8. A monitor in accordance with claim 6, wherein:
   said control unit compares present said signals from said first sensor with present signals from said second sensor to determine a reliability of the first or second estimations of the respiration rate.

9. A monitor in accordance with claim 6, wherein:
   said quality value setting means measures a signal to noise ratio of one of said first and second sensors, and uses said signal to noise ratio to determine a respective said quality value.

10. A monitor in accordance with claim 6, wherein:
    said quality value setting means measures movement of the subject that would interfere with the sensing of one of the first and second sensors, said quality value setting means uses the measurements of movement to determine a respective said quality value.

11. A monitor in accordance with claim 6, wherein:
    said quality value setting means measures external sound from around the subject that would interfere with the sensing of one of the first and second sensors, said quality value setting means uses the measurements of sound to determine a respective said quality value.

12. A monitor in accordance with claim 6, wherein:
    said quality value setting means includes an evaluating sensor for sensing the evaluating information from the subject, said evaluating sensor being separate from said first sensor and said second sensor.

13. A monitor in accordance with claim 12, wherein:
    one of said first sensor and said second sensor measures the respiration rate by measuring a first type of physical movement of the patient;

said evaluating sensor measures a second type of physical movement of the patient, the second type of physical movement being different than the first type of physical movement.

14. A monitor in accordance with claim 6, wherein:
said quality value setting means includes an evaluating sensor for sensing evaluating information from the subject, said evaluating information includes information concerning a wave shape of the signal received from one of said first sensor and said second sensor.

15. A monitor in accordance with claim 6, wherein:
said quality value setting means includes an evaluating sensor for sensing evaluating information from the subject, said evaluating information includes information concerning an amplitude spectrum of the signal received from one of said first sensor and said second sensor.

16. A monitor in accordance with claim 6, wherein:
said quality value setting means includes an evaluating sensor for sensing evaluating information from the subject, said evaluating information includes information concerning a frequency spectrum of the signal received from one of said first sensor and said second sensor.

\* \* \* \* \*